(12) United States Patent
Zon et al.

(10) Patent No.: US 8,101,412 B2
(45) Date of Patent: *Jan. 24, 2012

(54) METHOD OF ENHANCING PROLIFERATION AND/OR HEMATOPOIETIC DIFFERENTIATION OF STEM CELLS

(75) Inventors: Leonard I Zon, Wellesley, MA (US); Alan J Davidson, West Roxbury, MA (US); George Q Daley, Weston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/191,402

(22) Filed: Aug. 14, 2008

(65) Prior Publication Data

US 2009/0004163 A1  Jan. 1, 2009

Related U.S. Application Data

(63) Continuation of application No. 10/528,808, filed as application No. PCT/US03/29185 on Sep. 18, 2003, now Pat. No. 7,427,603.

(60) Provisional application No. 60/413,816, filed on Sep. 26, 2002.

(51) Int. Cl.
*A61K 48/00* (2006.01)

(52) U.S. Cl. ............ 435/467; 435/377; 435/235.1; 514/44 R

(58) Field of Classification Search ............ None
See application file for complete search history.

(56) References Cited

U.S. PATENT DOCUMENTS

| 6,498,018 | B1 | 12/2002 | Carpenter |
| 6,645,763 | B2 | 11/2003 | Kobayashi et al. |
| 6,777,233 | B2 | 8/2004 | Carpenter |
| 7,427,603 | B2 * | 9/2008 | Zon et al. ............ 514/44 R |

OTHER PUBLICATIONS

Kennedy et al. A common precursor for primitive erythropoiesis and definitive haematopoiesis, Nature, Apr. 3, 1997, vol. 386:488-493.
Chen et al. Analysis of Hoxa7/Hoxb7 mutants suggests periodicity in the generation of the different sets of vertebrae, Mechanisms of Development, (1998), vol. 77:49-57.
Kappen, Claudia Disruption of the Homeobox Gene Hoxb-6 in Mice Results in Increased Numbers of Early Erythrocyte Progenitors, American Journal of Hematology (2000), vol. 65:111-118.
Lawrence et al. Mice Bearing a Targeted Interruption of the Homeobox Gene HOXA9 Have Defects in Myeloid, Erythroid, and Lymphoid Hematopoiesis, Blood (1997), vol. 89:1922-1930.
Chase et al. Fusion of ETV6 to the Caudal-Related Homeobox Gene CDX2 in Acute Myeloid Leukemia with the t (12;13)(p13;q12), Blood, Feb. 1, 1999, vol. 93, 1025-1031.
Kingsley et al., Subtractive hybridization reveals tissue-specific expression of ahnak during embryonic development, Develop. Growth Differ., vol. 43, 133-143, (2001).
Beck et al., Developmental Dynamics, vol. 204, 1995, pp. 219-227.
Lewis, E. B. A Gene Complex Controlling Segmentation in *Drosophila* Nature (Dec. 7, 1978), vol. 276, 565-570.
Buske and Humphries Homeobox Genes in Leukemogenesis, International Journal of Hematology, (2000), vol. 71, 301-308.
Kimmel et al. Origin and Organization of the Zebrafish Fate Map, Development (1990), vol. 108, 581-594.
Hammerschmidt et al. Genetic analysis of dorsoventral pattern formation in the zebrafish: requirement of BMP-like ventralizing activity and its dorsal repressor Genes & Development (1996), vol. 10, 2452-2461.
Sauvageau et al. Overexpression of HOXB4 in hematopoietic cells causes the selective expansion of more primitive populations in vitro and in vivo, Genes & Development (1995), vol. 9:1753-1765.
Krauss et al. Expression of the zebrafish paired box gene pax[zf-b] during early neurogenesis, Development (1991), vol. 113, 1193-1206.
Joly et al. Expression of a zebrafish caudal homeobox gene correlates with the establishment of posterior cell lineages at gastrulation, Differentiation (1992), vol. 50: 75-87.
Mlodzik et al. Isolation of caudal, a *Drosophila* homeo box-containing gene with maternal expression, whose transcripts form a concentration gradient at the pre-blastoderm stage, The EMBO Journal (1985), vol. 4 No. 11: 2961-2969.
Perkins and Cory Conditional immortalization of mouse myelomonocytic, megakaryocytic and mast cell progenitors by the HOX-2.4 homeobox gene, The EMBO Journal (1993), vol. 12 No. 10:3835-3846.
Choi, Kyunghee, The Hemangioblast: A Common Progenitor of Hematopoietic and Endothelial Cells, Journal of Hematotherapy & Stem Cell Research (2002), vol. 11: 91-101.
Struhl, Gary, Genes Controlling Segmental Specification in the *Drosophila* Thorax, Proc. Natl. Acad. Sci. USA (1982) vol. 79, 7380-7384.

(Continued)

*Primary Examiner* — Jim Ketter
(74) *Attorney, Agent, or Firm* — Nixon Peabody LLP; David S. Resnick; Leena H. Karttunen Contarino

(57) ABSTRACT

The present invention provides a method for enhancing the proliferation and/or hematopoietic differentiation and/or maintenance of mammalian stem cells. The method is useful for generating expanded populations of hematopoietic stem cells (HSCs) and thus mature blood cell lineages. This is desirable where a mammal has suffered a decrease in hematopoietic or mature blood cells as a consequence of disease, radiation or chemotherapy. The method of the present invention comprises increasing the intracellular level of a cdx in stem cells, including hematopoietic stem cells, in culture, either by providing an exogenous cdx protein to the cell, or by introduction into the cell of a genetic construct encoding a cdx. The cdx is selected from the cdx family and includes cdx1, cdx2, or cdx4. The cdx may be a wild type protein appropriate for the species from which the cells are derived, or a mutant form of the protein.

13 Claims, 5 Drawing Sheets

OTHER PUBLICATIONS

Hunt and Krumlauf Deciphering the Hox Code: Clues to patterning branchial regions of the head, Cell, Sep. 20, 1991, vol. 66:1075-1076.
Owens and Hawley HOX and Non-HOX Homeobox Genes in Leukemic Hematopoiesis, Stem Cells, (2002), vol. 20:364-379.
Choi et al. A common precursor for hematopoietic and endothelial cells, Development (1998), vol. 125:725-732.
Gering et al. The SCL gene specifies haemangioblast development from early mesoderm, The EMBO Journal (1998), vol. 17:4029-4045.
Liao et al., SCL/Tal-1 transcription factor acts downstream of cloche to specify hematopoietic and vascular progenitors in zebrafish, Genes & Development (1998), vol. 12:621-626.
Shivdasani et al., Absence of blood formation in mice lacking the T-cell leukaemia oncoprotein tal-1/SCL, Nature, Feb. 2, 1995, vol. 373:432-434.
Robb et al., Absence of yolk sac hematopoiesis from mice with a targeted disruption of the scl gene, Proc. Natl. Acad. Sci. USA, (1995) vol. 92:7075-7079.
Warga and Nusslein-Volhard, Origin and development of the zebrafish endoderm, Development (1999), vol. 126:827-838.
Krumlauf, Robb, Hox Genes in Vertebrate Development, Cell, Jul. 29, 1994, vol. 78:191-201.
Carè et al., Enforced expression of HOXB7 promotes hematopoietic stem cell proliferation and myeloid-restricted progenitor differentiation, Oncogene (1999) vol. 18:1993-2001.
Thorsteinsdottir et al., Overexpression of the myeloid leukemia-associated Hoxa9 gene in bone marrow cells induces stem cell expansion, Blood, Jan. 1, 2002, vol. 99: 121-129.
Antonchuk et al. HOXB4-Induced Expansion of Adult Hematopoietic Stem Cells Ex Vivo, Cell, Apr. 5, 2002, vol. 109:39-45.
Kyba et al. HoxB4 Confers Definitive Lymphoid-Myeloid Engraftment Potential on Embryonic Stem Cell and Yolk Sac Hematopoietic Progenitors, Cell, Apr. 5, 2002, vol. 109, 29-37.
Kroon et al. Hoxa9 transforms primary bone marrow cells through specific collaboration with Meis 1a but not Pbx1b, EMBO J. (1998) vol. 17, No. 13, 3714-3725.
Thorsteinsdottir et al. Overexpression of HOXA10 in Murine Hematopoietic Cells Perturbs both Myeloid and Lymphoid Differentiation and Leads to Acute Myeloid Leukemia, Molecular and Cellular Biology, Jan. 1997, vol. 17:495-505.
Nakamura et al. Cooperative activation of Hoxa and Pbx1-related genes in murine myeloid leukaemias, Nature Genetics, Feb. 1996, vol. 12:149-153.
Lam and Aplan NUP98 gene fusions in hematologic malignancies, Leukemia (2002), vol. 15:1689-1695.
Ziemin-Van Der Poel et al., Identification of a gene, MLL, that spans the breakpoint in 11q23 translocations associated with human leukemias, Proc. Natl. Acad. Sci., USA Dec. 1991, vol. 88:10735-10739.
Hammerschmidt et al., Mutations affecting morphogenesis during gastrulation and tail formation in the zebrafish, Danio rerio, Development, (1996) vol. 123:143-151.
Bennett et al., Myelopoiesis in the zebrafish, Danio rerio, Blood, Aug. 1, 2001, vol. 98:643-651.
Lieschke et al., Morphologic and functional characterization of granulocytes and macrophages in embryonic and adult zebrafish, Blood, Nov. 15, 2001, vol. 98:3087-3096.
Serluca and Fishman Pre-pattern in the pronephric kidney field of zebrafish, Development, (2002) vol. 128:2233-2241.
Chong et al. Expression pattern of two zebrafish genes, cxcr4a and cxcr4b, Mechanisms of Development (2001), vol. 109:347-354.
Hild et al. The smad5 mutation somitabun blocks Bmp2b signaling during early dorsoventral patterning of the zebrafish embryo, Development (1999), vol. 126, 2149-2159.
Postlethwait et al. Vertebrate genome evolution and the zebrafish gene map, Nature Genetics, Apr. 1998, vol. 18:345-349.
Katsuyama et al. Ascidian Tail Formation Requires caudal Function, Developmental Biology (1999), vol. 213:257-268.
Edgar et al. Zygotic Expression of the caudal Homolog pal-1 Is Required for Posterior Patterning in *Caenorhabditis elegans* Embryogenesis, Developmental Biology (2001), vol. 229, 71-88.
Subramanian et al. Disruption of the Murine Homeobox Gene Cdx1 Affects Axial Skeletal Identities by Altering the Mesodermal Expression Domains of Hox Genes, Cell, Nov. 17, 1995, vol. 83: 641-653.
Chawengsaksophak et al., Homeosis and intestinal tumours in Cdx2 mutant mice, Nature, Mar. 6, 1997, vol. 386:84-87.
Van den Akker et al. Cdx1 and Cdx2 have overlapping functions in anteroposterior patterning and posterior axis elongation, Development, (2002) vol. 129:2181-2193.
Beck et al. Reprogramming of intestinal differentiation and intercalary regeneration in Cdx2 mutant mice, Proc. Natl. Acad. Sci USA, Jun. 1999, vol. 96:7318-7323.
Tamai et al. Colonic Hamartoma Development by Anomalous Duplication in Cdx2 Knockout Mice, Cancer Research, Jun. 15, 1999, vol. 59:2965-2970.
Charité et al., Transducing positional information to the Hox genes: critical interaction of cdx gene products with position-sensitive regulatory elements, Development (1998), vol. 125:4349-4358.
Hunter et al. Hox gene expression in a single Caenorhabditis elegans cell is regulated by a caudal homolog and intercellular signals that inhibit Wnt signaling, Development (1999), vol. 126:805-814.
Isaacs et al. Regulation of Hox gene expression and posterior development by the Xenopus caudal homologue Xcad3, The EMBO Journal (1998), vol. 17, No. 12, 3413-3427.
McGrath and Palis Expression of Homeobox Genes, Including an Insulin Promoting Factor, in the Murine Yolk Sac at the Time of Hematopoietic Initiation, Molecular Reproduction and Development (1997), vol. 48:145-153.
Buske et al. Deregulated expression of HOXB4 enhances the primitive growth activity of human hematopoietic cells Blood (2002), vol. 100:862-868.
Björnsson et al. Reduced Proliferative Capacity of Hematopoietic Stem Cells Deficient in Hoxb3 and Hoxb4, Molecular and Cellular Biology, Jun. 2003, vol. 23:3872-3883.

\* cited by examiner

METHOD OF ENHANCING PROLIFERATION AND/OR HEMATOPOIETIC DIFFERENTIATION OF STEM CELLS

CROSS-REFERENCE TO RELATED APPLICATIONS

This application is a Continuation application of a co-pending U.S. application Ser. No. 10/528,808, filed Mar. 23, 2005, which is U.S. National Stage Entry under 35 U.S.C. §371 of International Application No. PCT/US03/29185, filed Sep. 18, 2003, which claims priority from U.S. Provisional Application No. 60/413,816, filed on Sep. 26, 2002.

BACKGROUND OF THE INVENTION

Chemo- and radiation therapies cause dramatic reductions in blood cell populations in cancer patients. At least 500,000 cancer patients undergo chemotherapy and radiation therapy in the US and Europe each year and another 200,000 in Japan. Bone marrow transplantation therapy of value in aplastic anemia, primary immunodeficiency and acute leukemia (following total body irradiation) is becoming more widely practiced by the medical community. At least 15,000 Americans have bone marrow transplants each year. Other diseases can cause a reduction in entire or selected blood cell lineages. Examples of these conditions include anemia (including macrocytic and aplastic anemia); thrombocytopenia; hypoplasia; immune (autoimmune) thrombocytopenic purpura (ITP); and HIV induced ITP.

Pharmaceutical products are needed which are able to enhance reconstitution of blood cell populations of these patients.

SUMMARY OF THE INVENTION

The present invention provides a method for enhancing the proliferation and/or hematopoietic differentiation and/or maintenance of mammalian stem cells. The method is useful for generating expanded populations of hematopoietic stem cells (HSCs) and thus mature blood cell lineages. This is desirable where a mammal has suffered a decrease in hematopoietic or mature blood cells as a consequence of disease, radiation or chemotherapy. The method of the present invention comprises increasing the intracellular level of a cdx in stem cells, including hematopoietic stem cells, in culture, either by providing an exogenous cdx protein to the cell, or by introduction into the cell of a genetic construct encoding a cdx. The cdx is selected from the cdx family and includes cdx1, cdx2, or cdx4. The cdx may be a wild type protein appropriate for the species from which the cells are derived, or a mutant form of the protein.

BRIEF DESCRIPTION OF THE DRAWINGS

FIG. 1 shows effect of cdx4 and HoxB4 overexpression on hematopoietic progenitors derived from embryoid bodies (EBs). Colony forming units scored are macrophage (Mac), megakaryocytes and mixed lineage (Meg-mix), granulocyte, macrophage (GM), and granulocyte, macrophage, megakaryocyte (GEMM). Photographs of representative colonies are shown below the graph.

FIG. 2 shows quantitative PCR analysis of the expression of selected HoxA, HoxB, and HoxC cluster genes in EBs overexpressing cdx4.

FIG. 3 shows RT-PCR analysis of cdx4 expression during EB development.

FIG. 4 shows the effect of cdx4 overexpression on hematopoietic development during different stages of EB development using tetracycline-inducible murine embryonic stem cell lines. cdx4 expression was induced by the addition of doxycycline between the days indicated below the graph and hematopoietic colony formation was assayed at day 6. The types of colonies scored were the same as above, which the addition of primitive and definitive erythroid colonies (Ery-P and Ery-D, respectively) and mast cell colonies (Mast).

FIG. 5 shows a model for the role of cdx4 in AP patterning and blood development. Signaling molecules such as FGFs, Wnts, and retinoic acid (RA) are known to regulate the expression of cdx4, which in turn establishes the correct expression domains of hox genes necessary for blood development. In the absence of cdx4 (right panel), hox expression domains are shifted and fewer erythroid cells are formed.

DETAILED DESCRIPTION OF THE INVENTION

Figure 1:
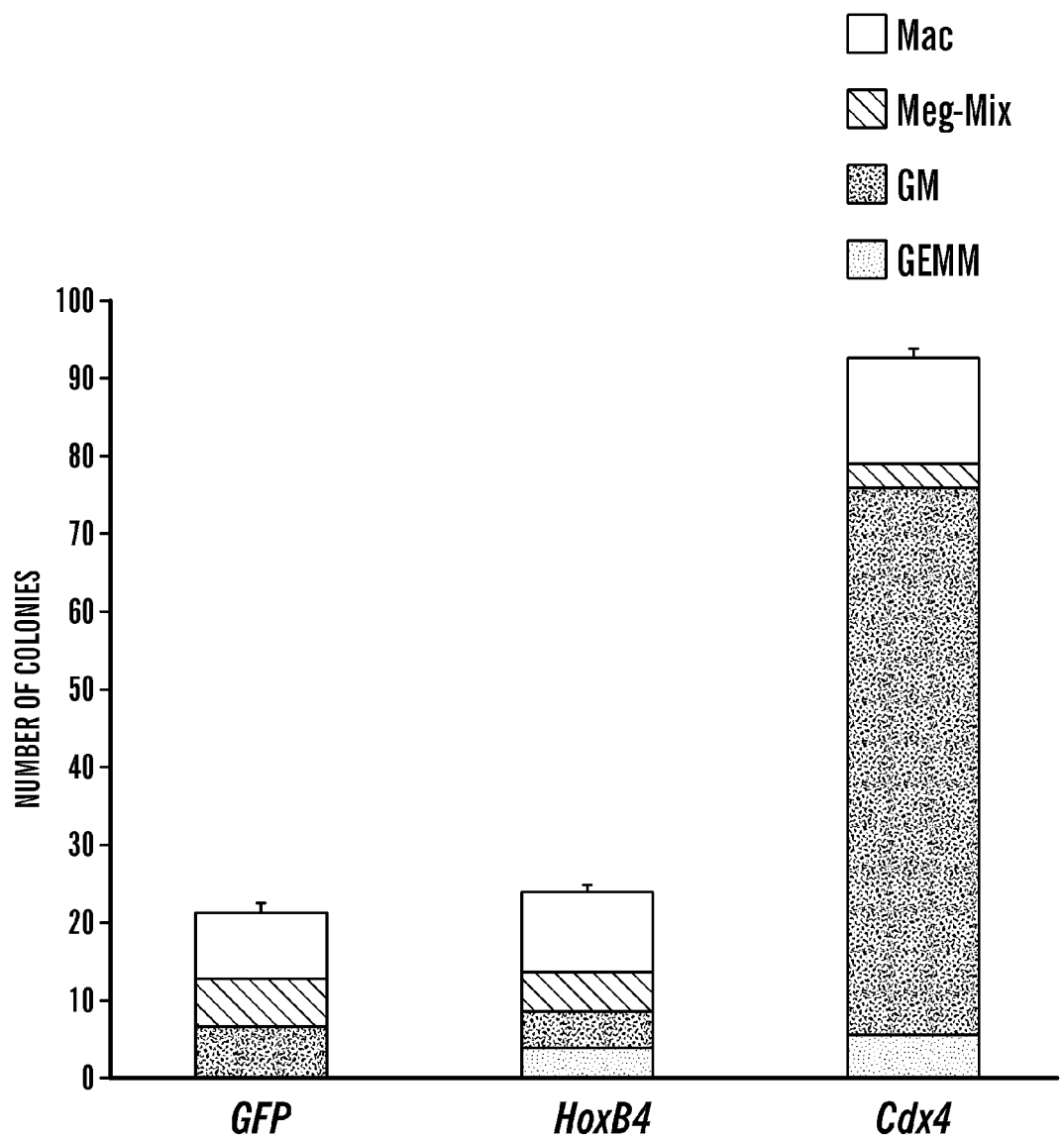
FIGS. 1-5 show that cdx4 alters hox gene expression in zebrafish and mouse cells and induces blood development in embryoid bodies.

The present invention provides a method for enhancing the proliferation and/or hematopoietic differentiation and/or maintenance of mammalian stem cells. The method is useful for generating expanded populations of hematopoietic stem cells (HSCs) and thus mature blood cell lineages. This is desirable where a mammal has suffered a decrease in hematopoietic or mature blood cells as a consequence of disease, radiation, chemotherapy or congenital anemia (e.g., Diamond Blackfan Anemia). The method of the present invention comprises increasing the intracellular level of a cdx in stem cells, including hematopoietic stem cells, in culture, either by providing an exogenous cdx protein to the cell, or by introduction into the cell of a genetic construct encoding a cdx. The cdx is selected from the cdx family and includes cdx1, cdx2, or cdx4. The cdx may be a wild type protein appropriate for the species from which the cells are derived, or a mutant form of the protein.

The differentiated and expanded cell populations are useful as a source of hematopoietic stem cells, which may be used in transplantation to restore hematopoietic function to autologous or allogeneic recipients.

In one embodiment, mammalian stem cells are differentiated to HSCs in vitro by increasing the level of cdx in the cell. In another embodiment, the number of HSCs in a culture is expanded by increasing the levels of cdx in the cell. The intracellular levels of cdx may be manipulated by providing exogenous cdx protein to the cell, or by introduction into the cell of a genetic construct encoding a cdx. The cdx may be a wild-type or a mutant form of the protein.

The term cdx, as used herein, is intended to refer to both wild-type and mutant forms of the cdx protein family, and to fusion proteins and derivatives thereof. Usually the protein will be of mammalian origin, although the protein from other species may find use. The sequences of many cdx proteins are publicly known. Preferably, the mammal is a human and the cdx is selected from the group consisting of cdx1 (GenBank accession number NM_001804; Suh et al., *J. Biol. Chem.* 277:35795 (2002)), cdx2 (GenBank accession number NM_001265; Yamamoto et al., Biochem. Biophys. Res. Commun. 300(4):813 (2003)), or cdx4 (GenBank accession number NM_005193; Horn et al., Hum. Mol. Genet. 4(6), 1041-1047 (1995)).

In one embodiment of the invention, the cdx is delivered to the targeted stem cells by introduction of an exogenous nucleic acid expression vector into the cells. Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc.

Retrovirus based vectors have been shown to be particularly useful when the target cells are hematopoietic stem cells. For example, see Baum et al. (1996) J Hematother 5(4):323-9; Schwarzenberger et al. (1996) Blood 87:472-478; Nolta et al. (1996) P.N.A.S. 93:2414-2419; and Maze et al. (1996) P.N.A.S. 93:206-210. Lentivirus vectors have also been described for use with hematopoietic stem cells, for example see Mochizuki et al. (1998) J Virol 72(11):8873-83. The use of adenovirus based vectors with hematopoietic cells has also been published, see Ogniben and Haas (1998) Recent Results Cancer Res 144:86-92.

Various techniques known in the art may be used to transfect the target cells, e.g. electroporation, calcium precipitated DNA, fusion, transfection, lipofection and the like. The particular manner in which the DNA is introduced is not critical to the practice of the invention.

Combinations of retroviruses and an appropriate packaging line may be used, where the capsid proteins will be functional for infecting the target cells. Usually, the cells and virus will be incubated for at least about 24 hours in the culture medium. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells.

The sequences at the 5' and 3' termini of the retrovirus are long terminal repeats (LTR). A number of LTR sequences are known in the art and may be used, including the MMLV-LTR; HIV-LTR; AKR-LTR; FIV-LTR; ALV-LTR; etc. Specific sequences may be accessed through public databases. Various modifications of the native LTR sequences are also known. The 5' LTR acts as a strong promoter, driving transcription of the cdx gene after integration into a target cell genome. For some uses, however, it is desirable to have a regulatable promoter driving expression. Where such a promoter is included, the promoter function of the LTR will be inactivated. This is accomplished by a deletion of the U3 region in the 3' LTR, including the enhancer repeats and promoter, that is sufficient to inactivate the promoter function. After integration into a target cell genome, there is a rearrangement of the 5' and 3' LTR, resulting in a transcriptionally defective provirus, termed a "self-inactivating vector".

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in hematopoietic cell types, e.g. IL-2 promoter in T cells, immunoglobulin promoter in B cells, etc.

In an alternative method, expression vectors that provide for the transient expression in mammalian cells may be used. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient short term expansion of cells, but do not affect the long term genotype of the cell.

In some cases it may be desirable to provide exogenous cdx protein, rather than transducing the cells with an expression construct. The cdx protein may be added to the culture medium at high levels. Preferably the cdx protein is modified so as to increase its transport into the cells. See, for example, US 2002/0086383.

In one embodiment of the invention, tat protein is used to deliver cdx. The preferred transport polypeptides are characterized by the presence of the tat basic region amino acid sequence (amino acids 49-57 of naturally-occurring tat protein); the absence of the tat cysteine-rich region amino acid sequence (amino acids 22-36 of naturally-occurring tat protein) and the absence of the tat exon 2-encoded carboxy-terminal domain (amino acids 73-86 of naturally-occurring tat protein). Transport polypeptides are attached to cdx by chemical cross-linking or by genetic fusion, where the cdx moiety may be a wild-type or stabilized form. A unique terminal cysteine residue is a preferred means of chemical cross-linking.

The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Stem cells can be derived from a human donor, e.g., pluripotent hematopoietic stem cells, adult somatic stem cells, and the like. Embryonic stem cells may also be used. Stem cells can also be obtained from umbilical cord blood, amniotic fluid, chorionic villus and placenta. See, WO03042405.

Other hematopoietic "progenitor" cells of interest include cells dedicated to lymphoid lineages, e.g. immature T cell and B cell populations. The methods of the present invention are useful in expanding selected populations of these cells.

Purified populations of stem or progenitor cells may be used to initiate the cultures. For example, human hematopoietic stem cells may be positively selected using antibodies specific for CD34, thy-1; or negatively selected using lineage specific markers which may include glycophorin A, CD3, CD24, CD16, CD14, CD38, CD45RA, CD36, CD2, CD19, CD56, CD66a, and CD66b.

The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

The cells which are employed may be fresh, frozen, or have been subject to prior culture. They may be fetal, neonate, adult. Hematopoietic cells may be obtained from fetal liver, bone marrow, blood, particularly G-CSF or GM-CSF mobilized peripheral blood, cord blood or any other conventional source. The manner in which the stem cells are separated from other cells of the hematopoietic or other lineage is not critical to this invention. As described above, a substantially homogeneous population of stem or progenitor cells may be obtained by selective isolation of cells free of markers associated with differentiated cells, while displaying epitopic characteristics associated with the stem cells.

The stem or progenitor cells are grown in vitro in an appropriate liquid nutrient medium. Generally, the seeding level will be at least about 10 cells/ml, more usually at least about 100 cells/ml and generally not more than about $10^5$ cells/ml, usually not more than about $10^4$ cells/ml.

Various media are commercially available and may be used, including Ex vivo serum free medium; Dulbecco's Modified Eagle Medium (DMEM), RPMI, Iscove's medium, etc. The medium may be supplemented with serum or with defined additives. Appropriate antibiotics to prevent bacterial growth and other additives, such as pyruvate (0.1-5 mM), glutamine (0.5-5 mM), 2-mercaptoethanol may also be included.

Culture in serum-free medium is of particular interest. The medium may be any conventional culture medium, generally supplemented with additives such as iron-saturated transferrin, human serum albumin, soy bean lipids, linoleic acid, cholesterol, alpha thioglycerol, crystalline bovine hemin, etc., that allow for the growth of hematopoietic cells.

Preferably the expansion medium is free of cytokines, particularly cytokines that induce cellular differentiation. The term cytokine may include lymphokines, monokines and growth factors. Included among the cytokines are thrombopoietin (TPO); nerve growth factors; platelet-growth factor; transforming growth factors (TGFs); erythropoietin (EPO); interferons such as interferon-α, β, and γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1γ, IL-2, IL-3, IL-4, IL-5, IL-6, IL-7, IL-8, IL-9, IL-11, IL-12; etc. In some circumstances, proliferative factors that do not induce cellular differentiation may be included in the cultures, e.g. c-kit ligand, LIF, and the like.

Frequently stem cells are isolated from biological sources in a quiescent state. Certain expression vectors, particularly retroviral vectors, do not effectively infect non-cycling cells. Cultures established with these vectors as a source of cdx sequences are induced to enter the cell cycle by a short period of time in culture with growth factors. For example, hematopoietic stem cells are induced to divide by culture with c-kit ligand, which may be combined with LIF, IL-11 and thrombopoietin. After 24 to 72 hours in culture with cytokines, the medium is changed, and the cells are exposed to the retroviral culture, using culture conditions as described above.

After seeding the culture medium, the culture medium is maintained under conventional conditions for growth of mammalian cells, generally about 37° C. and 5% $CO_2$ in 100% humidified atmosphere. Fresh media may be conveniently replaced, in part, by removing a portion of the media and replacing it with fresh media. Various commercially available systems have been developed for the growth of mammalian cells to provide for removal of adverse metabolic products, replenishment of nutrients, and maintenance of oxygen. By employing these systems, the medium may be maintained as a continuous medium, so that the concentrations of the various ingredients are maintained relatively constant or within a pre-described range. Such systems can provide for enhanced maintenance and growth of the subject cells using the designated media and additives.

These cells may find various applications for a wide variety of purposes. The cell populations may be used for screening various additives for their effect on growth and the mature differentiation of the cells. In this manner, compounds which are complementary, agonistic, antagonistic or inactive may be screened, determining the effect of the compound in relationship with one or more of the different cytokines.

The populations may be employed as grafts for transplantation. For example, hematopoietic cells are used to treat malignancies, bone marrow failure states and congenital metabolic, immunologic and hematologic disorders. Marrow samples may be taken from patients with cancer, and enriched populations of hematopoietic stem cells isolated by means of density centrifugation, counterflow centrifugal elutriation, monoclonal antibody labeling and fluorescence activated cell sorting. The stem cells in this cell population are then expanded in vitro and can serve as a graft for autologous marrow transplantation. The graft will be infused after the patient has received curative chemo-radiotherapy.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

EXAMPLES

Introduction

The formation of blood cells during vertebrate development occurs in successive stages in anatomically distinct sites[6]. In amniotes, the first wave (known as primitive or embryonic hematopoiesis) originates in the yolk sac blood islands and is characterized by the formation of erythroid and endothelial cells. The coincident onset of both hematopoiesis and vasculogenesis in the yolk sac has led to the hypothesis that both cell types are derived from a common precursor, termed the hemangioblast[7]. In zebrafish, embryonic hematopoiesis occurs in an intra-embryonic location known as the intermediate cell mass (ICM). The ICM develops along the trunk midline by the convergence of bilateral stripes of hematopoietic and vascular precursors. One of the earliest molecular markers of these ICM precursors is the stem cell leukemia (scl) gene, which encodes a basic helix-loop-helix transcription factor[8,9]. Gene targeting studies in mice have demonstrated that scl is necessary for the development of all hematopoietic lineages. In contrast, endothelial cells are present in scl null embryos but fail to remodel properly in the yolk sac[10,11]. Studies in zebrafish have shown that overexpression of scl during development is sufficient to induce ectopic blood and vascular cells and these findings have led to the suggestion that scl is capable of specifying hemangioblast fate from mesoderm[8].

While fate-mapping studies in zebrafish have shown that embryonic blood cells arise from ventral mesoderm of the late blastula[12,13] the molecular pathways responsible for inducing the early expression of scl are largely unknown. In general, posterior tissues of mesodermal origin are derived from ventral mesoderm whereas anterior tissues descend from more dorsal mesoderm. Consistent with this, genes that 'ventralize' the early gastrula embryo, such as the bone morphogenetic proteins (BMPs), induce an expansion of blood and posterior tissues at the expense of more anterior structures such as the head[14]. Thus, factors that determine posterior cell fates along the anteroposterior (AP) axis must also be intimately connected with genes that specify ventral fates including blood.

The establishment of tissues along the AP axis of the embryo is dependent upon the homeobox transcription factors encoded by the hox genes[15]. Within the genome, these genes are grouped together in clusters (HoxA, HoxB, HoxC and HoxD) and are expressed in overlapping domains along the AP axis with their anterior expression limits correlating to their physical order within the cluster. Perturbations in these anterior expression boundaries result in changes in cell fate and this has led to the 'Hox code' hypothesis, in which specific combinations of Hox genes are believed to specify tissue identities along the AP axis[15]. Despite being held as critical regulators of embryonic patterning, the effects of germline disruptions of Hox genes in the mouse are largely restricted to the axial skeleton, neural crest, central nervous system, and limbs[3,15]. The relatively mild phenotypes of single Hox gene knockouts in mice can be explained by extensive functional redundancy between paralogous genes within each cluster.

A number of studies have demonstrated that ectopically expressed hox genes can influence hematopoietic lineage decisions[4,5]. For example, overexpression of HoxA9, HoxB4, and HoxB7 has been shown to modulate the proliferation/self-renewal of mouse hematopoietic stem cells[16-19]. In addition, ectopically expressed HoxB4 can induce embryonic hematopoietic progenitors to acquire properties characteristic of adult hematopoietic stem cells[20]. Deregulated Hox gene expression is also associated with leukemia transformation[4,5]. Overexpression of HoxA9[18,21] or HoxA10[22] in murine bone marrow ultimately leads to acute myeloid leukemia (AML) whereas proviral activation of HoxA7 has been implicated in myeloid leukaemia[23]. A subset of human AML is associated with a fusion of the NUP98 gene, which encodes a component of the nuclear pore complex, to a number of different HOX genes including HOXA9[24]. Translocations involving the MLL gene, a homologue of MLL that is required for the maintenance of HOX gene expression, have also been implicated in certain human leukemias[25].

In this study we have characterized the zebrafish kugelig (kgg) mutant, which exhibits reduced scl expression, severe anemia, and a shortened AP axis. We identify the kgg locus as the caudal-related homeobox gene cdx4 and show that the defect in erythropoiesis is associated with aberrant hox gene expression. Overexpressing scl in kgg mutants fails to rescue blood development indicating that the specification of hematopoeitic cell fate is dependent upon cdx4 function. In contrast, erythropoiesis in kgg mutants can be robustly rescued by overexpressing hoxb7a and hoxa9a but not hoxb8a, suggesting that the hematopoietic defects result directly from perturbations in hox gene expression. Overexpression of cdx4 during zebrafish development or in mouse embryonic stem cells induces blood formation and alters hox gene expression patterns. Taken together, our findings demonstrate that cdx4 is both necessary and sufficient for the formation of embryonic blood cells during vertebrate development.

Example 1

Methods

Computer analysis. The genetic map position of kgg was obtained from the Max-Planck-Institut für Entwicklungsbiologie (Tübingen, Germany) website. Genomic sequence of the cdx4 locus was obtained from the Wellcome Trust Sanger Institute website. RH mapping data was provided by the Children's Hospital Genome Initiative (Boston, Mass.) website. Protein sequence prediction and alignment were performed using DNAstar software.

Deletion analysis and genotyping. The following primers to each exon of the cdx4 gene were used to determine the extent of the kgg$^{tv205}$ deletion by PCR: exon one (forward 5'-AGCTCCTTTTGGACTATTAC-3' (SEQ ID NO: 1); reverse 5'-CCAACGTACATGATTTGGAA-3' (SEQ ID NO: 2)), exon two (forward 5'-ATACCTTTTGGAGAAAGAGG-3' (SEQ ID NO: 3); reverse 5'-CCGGTTGATGACGACTG-GAC-3' (SEQ ID NO: 4)), exon three (forward 5'-CAAAAC-GAGAACGAAGGAGA-3' (SEQ ID NO: 5); reverse 5'-ACCTGTCTCTCTGAAAGCCC-3' (SEQ ID NO: 6)), and exon four (forward 5'-TAAGATCTGGTTTCAGAACC-3' (SEQ ID NO: 7); reverse 5'-TGGATGATCCAAGTTC-GAGT-3' (SEQ ID NO: 8)). Exon three forward and exon four reverse primers were used to genotype kgg$^{tv205}$ embryos. Primers specific to the ESTs fj63c09, fb79h04, flk1 (fk52c05), fb75e05, chic1 (fj33g02), fc54b04, and fi30c11 were obtained from the WashU Zebrafish Genome Resources Project website, while primer sequences for the markers z20545 and z11437 were obtained from the Massachusetts General Hospital Zebrafish Server website. 3' rapid amplification of cDNA ends (RACE) was performed using the SMART RACE kit (Clontech), cDNA prepared from 14-15 somite stage kgg$^{tv205}$ mutants, and the cdx4-specific primer 5'-AGCCTCGGACCTCCAAATTC-3' (SEQ ID NO: 9). PCR products were subcloned in the pGEM-T easy vector (Promega, Madison, Wis.) and sequenced.

Electrophoretic mobility shift assays. EMSAs were performed using the Gel Shift Assay System (Promega, Madison, Wis.) and in vitro translated (IVT) proteins prepared using the TNT SP6 Quick Coupled Transcription/Translation System (Promega, Madison, Wis.). Double-stranded oligonucleotide probes contained a single consensus cdx binding site (5'-GAGAAATTTATATTGT-3' (SEQ ID NO: 10); binding site consensus is underlined) or mutated site (5'-GAGAAATCCATATTGT-3' (SEQ ID NO: 11); mutated nucleotides are underlined).[35] S-methionine-labelled IVT cdx4 (wt) and the F(170)L mutant proteins were resolved on a 10-20% Tris-HCl polyacrylamide gel (Ready Gels, Biorad, Hercules, Calif.) alongside prestained broad range standards (Biorad) and analyzed by autoradiography.

Fish strains. The kgg[tv205] and kgg[tl240] mutant lines were obtained from the Tübingen stock center (Tübingen, Germany) and exhibit a similar severity of phenotype. Wild-type strains were AB, Tü, and WIK. Fish maintenance, breeding, and embryo staging were performed according to standard procedures.

Inducible cdx4 ES cell lines and colony assays. The inducible cdx4-targeting plasmid (plox-cdx4) was generated by subcloning mouse cdx4 into the EcoRI/XbaI site of the plox vector[20]. To make the tetracycline-inducible cdx4 ES cell line, Ainv15 ES cells were electroporated with 20 ug of plox-cdx4 and 20 ug of pSalk-Cre, followed by selection with G418 (400 ug/ml) in ES culture medium. Colonies positive for plox-cdx4 were confirmed by RT-PCR. The tetracycline-inducible cdx4 ES cells and EBs were maintained and produced as described previously[20]. Briefly, day 2 EBs from hanging-drops were harvested and cultured in rotating Petri dishes. Doxycycline was added into EB medium for the indicated time periods and then removed by three washes of PBS, followed by ES culture medium. EBs were collected at day 6 by collagenase treatment and plated into Methocult GF M3434 (StemCell Technologies). The colonies were scored 6-9 days later.

Microinjection. Wild-type and F(170)L mutant cdx4 cDNAs were subcloned into the expression vector pCS2+, linearized with NotI, and synthetic mRNA made using the mMessage mMachine kit (Ambion, Austin, Tex.). Capped RNA was resuspended in sterile water and 500 pl was injected between the one- to four-cell stages at a concentration of 30 ng/µl. Full-length hoxb6b, hoxb7a hoxb8a, and hoxa9a were amplified from 5-somite stage cDNA by RT-PCR using forward (hoxb6b: 5'-ATGCGAATTCCCCATGAGTTC-CTATTTCGTCA-3' (SEQ ID NO: 12); hoxb7a: 5'-ATGC-GAATTCACCATGAGTTCATTGTATTATGCG-3' (SEQ ID NO: 13); hoxb8a: 5'-ATGCGAATTCACCATGAGCT-CATATTTCGTCAAC-3' (SEQ ID NO: 14); hoxa9a: 5'-AT-GCGAATTCACCATGTCGACATCCGGAGCT-3' (SEQ ID NO: 15); start codon underlined)) and reverse (hoxb6b: 5'-GCATCTCGAGCTACATTCTACATGTTATGTAC-3' (SEQ ID NO: 16); hoxb7a: 5'-GACTCTCGAGCTACTCAT-CATCTTCTTCTTC-3' (SEQ ID NO: 17); hoxb8a: 5'-GCATCTCGAGCTACATTTGTTTTGCCTTGTC-3' (SEQ ID NO: 18); hoxa9a: 5'-GATCTCTAGATTAGTCTTC-CTTCGTTTC-3' (SEQ ID NO: 19); stop codon underlined) primers and subcloned (along with scl) into pCS2+. Synthetic mRNAs were prepared as above and 500 pl was injected at a concentration of 200, 6 and 2-4 ng/µl, for scl, hoxb7a/hoxa9a, and hoxb6b/hoxb8a, respectively. The cdx4 morpholinos (CGTACATGATTTGGAAGAAACCCCT (SEQ ID NO: 20); start codon underlined) were obtained from Gene Tools LLC (Corvallis, Oreg.) and solubilized in 1× Danieau solution (58 mM NaCl, 0.7 mM KCl, 0.4 mM MgSO4, 5 mM HEPES, pH 7.6) at a stock concentration of 35 mg/ml. One- to four-cell stage embryos were injected with 1 nl of cdx4 morpholino or an unrelated control morpholino (provided by Gene Tools LLC) at a concentration of 0.2 mg/ml. Injections were performed on a PLI-100 microinjector (Medical systems corp., NY).

Mutation analysis by RT-PCR. Total RNA was prepared from kgg[tv205] and kgg[tl240] mutant and wild-type embryos at 24 h.p.f. using established procedures and reverse transcribed using Superscript II RNAse H-reverse transcriptase (Invitrogen, Carlsbad, Calif.). The cdx4 ORF was amplified using forward (5'-CATGTACGTTGGATACCTTTTGG-3' (SEQ ID NO: 21)) and reverse (5'-TCCACAACCCACGCCTCT-TATT-3' (SEQ ID NO: 22)) primers, subcloned into the pGEM-T easy vector (Promega, Madison, Wis.) and sequenced. Our cDNA sequence of wild-type cdx4 differs from the published sequence (Genbank accession number NM_131109) by the addition of two cytosine nucleotides at +709-710. These extra nucleotides are also found in the cdx4 genomic sequence deposited in the Sanger Center database. The resulting frameshift changes the open reading frame of the carboxy terminus to give a predicted protein of 271 residues rather than the published length of 301 resides[32]. The F(170)L mutation of the kgg[tl240] allele was confirmed by sequencing six independent clones.

Radiation hybrid mapping. The cdx4 gene was mapped onto the Goodfellow RH panel by the Children's Hospital Genome Initiative group (Boston, Mass.) using the following forward (5'-AGGCGTGGGTTGTGGATTAC-3' (SEQ ID NO: 23)) and reverse (5'-GATACACTCACCACATACAG-3' (SEQ ID NO: 24)) primers. The contig encoding the foreign exon spliced onto exon 2 of cdx4 in kgg[tl240] mutants was mapped using forward (5'-GTGATCAACAACACGTCC-3' (SEQ ID NO: 25)) and reverse primers (5'-GGAATCTCCT-GTCAGCTG-3' (SEQ ID NO: 26)).

Retroviral expression of cdx4 in ES cells and quantitative PCR. Murine cdx4 was subcloned into the retroviral expression vector MSCV-IRES-GFP (pMIG) and retroviruses were generated using an ecotropic packaging vector and co-transfection to make viral supernatents. Embryoid bodies were formed from wild-type (RW4) ES cells by differentiating for 6 days and then definitive hematopoietic cells were enriched using an anti-CD41 magnetic strategy resulting in a 10-fold enrichment of CD41/c-Kit$^+$ cells. Approximately one million enriched cells were plated on OP9 monolayers in a 6-well dish and subjected to two rounds of retroviral infection with either GFP only or cdx4/GFP retroviral supernatants. After 48 hours, GFP$^+$ cells were sorted and were either directly lysed in Trizol (Invitrogen, Carlsbad, Calif.) for RNA preparation, or were plated in methylcellulose (M3434, StemCell Technologies) and scored for colony types 3-7 days later. Representative colonies were cytospun and stained using Jorvet J-322 Dip Quik, (Jorgensen Laboratories Inc., Loveland, Colo.). To quantitate the relative level of Hox gene mRNA, random hexamer-primed cDNA was prepared from total RNA from either GFP expressing or cdx4/GFP-expressing cells. Real time PCR measurements were performed with an ABI Prism 7700 Sequence Detector and dual labeled probes (sequence available on request), with the exception of HoxB4, which was quantitated using Sybr green reagents (Applied Biosystems). PCR reactions were performed in triplicate with internal references (GAPDH) used to normalize samples. Hox expression levels are expressed in arbitrary units (relative to the lowest sample) using the comparative $C_T$ method.

In situ hybridization and sectioning. In situ hybridization of mouse embryos was performed as previously described[56]. Whole mount In situ hybridization of zebrafish embryos was performed with double staining using the red substrate BCIP-INT. Embryos were fixed overnight in 4% paraformaldehyde, transferred to glycerol, flat-mounted under glass coverslips when possible, and photographed. The following riboprobes were used: cdx4, cxcr4, flk1, fli1, gata1, globin e3, hoxb5a, hoxb6b, hoxb7a, hoxb8a, hoxa9a, myoD, par1, pax2.1, runx1, scl, and wt1. Full-length cDNAs of the following hox genes were isolated by RT-PCR from 5-somite stage cDNA and subcloned into pCS2+ for riboprobe synthesis: hoxb4 (forward 5'-ATGCGAATTCACCATGGCCATGAGTTC-CTATTTG-3' (SEQ ID NO: 27); reverse 5'-GCATCTC-GAGCTATAGACTTGGCGGAGGTCC-3' (SEQ ID NO: 28)), hoxb8b (forward 5'-ATGCGAATTCACCATGAGT-TCCTACTTCGTCAAT-3' (SEQ ID NO: 29); reverse 5'-GCATCTCGAGCTATTTAGAATTGCTAGAAGC-3' (SEQ ID NO: 30)). Embryos to be sectioned were infiltrated in JB-4 resin, cut at a thickness of 5 μm, and then counterstained in 0.5% Safranin O before being mounted.

Results

Characterization of the kgg Mutant

We found that embryos homozygous for kugelig (kgg), an autosomal recessive mutation that was initially identified due to tail defects[26], exhibit severe anemia within the first day of development. Two kgg alleles, kgg$^{tv205}$ and kgg$^{t240}$, of equal severity have been isolated[26]. Although blood cell numbers begin to recover by 5 days post-fertilization (d. p. f), all mutants die between 7-10 d. p. f. To investigate the hematopoietic defect in kgg, we examined the expression of scl, gata1, and runx1. At the 5-somite stage, the bilateral stripes of scl$^+$ cells are thinner in kgg$^{tv205}$ embryos compared to wild-type (wt) controls. In addition, kgg$^{tv205}$ mutants show a decreased number of gata1$^+$ erythroid precursors and a complete absence of runx1 expression in blood and neuronal cells. Consistent with the neuronal loss of runx1 expression there are reduced numbers of Rohon-Beard cells at later stages. By 24 hours post-fertilization (h. p. f.), kgg$^{tv205}$ mutants have a severe reduction in the number of globin-expressing erythroid cells compared to wt siblings. In contrast, normal numbers of pu.1$^+$ myeloid cells[27,28] are formed from the cephalic mesoderm in kgg$^{tv205}$ embryos. Similarly, markers of definitive hematopoietic lineages, such as c-myb and rag1, are expressed in kgg$^{tv205}$ mutants at 36 h. p. f and 6 d. p. f., respectively. To study the development of the vasculature in the mutant, we examined the expression of the VEGF receptor, flk1. At the 10- and 15-somite stages, kgg$^{tv205}$ embryos have relatively normal numbers of angioblasts, although their convergence to the midline is delayed. By 24 h. p. f., the vasculature appears well formed in the mutants and the few blood cells that develop circulate normally. The pronephric kidney arises from mesoderm adjacent to the ICM precursors[29]. In kgg$^{tv205}$ mutants, the expression domains of the pronephric duct markers pax2.1[30] and cxcr4b[31] are shortened, although unlike the scl stripes, the width of the pax2.1 stripe is unaffected. Transcripts for the glomerulus marker wt1[29], which are normally expressed in mesoderm adjacent to somites one through four, extend from somites one through six in kgg$^{tv205}$ embryos suggesting that the kgg$^{tv205}$ mutation leads to an expansion of anterior kidney fates at the expense of more posterior fates. Other structures such as the head, notochord, and somites appear grossly normal in kgg$^{tv205}$ embryos, although the length of the embryo is shortened compared to wt embryos.

Identification of cdx4 as the Gene Defective in kgg Mutants

The kgg mutation maps to linkage group 14 near a number of candidate genes including cdx4[32], smad5[33], and wnt8[34]. An analysis of the cDNA sequence of wnt8 and smad5 from kgg mutants did not identify any mutations. cdx4 belongs to the caudal family of homeobox genes that have been implicated in AP patterning[35-37]. Three caudal paralogues exist in mammals (cdx1, cdx2, and cdx4) and mouse gene-targeting studies of cdx1 and cdx2 (cdx4 has yet to be targeted) have demonstrated a role for these genes in the AP patterning of the axial skeleton[38-40]. In addition, cdx2$^{+/-}$ mice develop hamartomatous polyps in the colon that result from a transformation of the intestinal epithelium to a more anterior (gastric) fate[39,41,42]. Sequence analysis of the cdx4 gene from kgg$^{t240}$ mutants revealed a T to A transversion in nucleotide +510, changing a conserved F(170) residue in the homeodomain to a leucine. This mutation prevents the protein from binding to a cdx4 consensus binding site in gel shift experiments. A partial deletion of the cdx4 gene, and at least one other neighboring gene (chic1), was found in kgg$^{tv205}$ mutants. To characterize this deletion in more detail we isolated the cdx4 transcript in kgg$^{tv205}$ mutants by 3' RACE and found that exon 2 had become spliced onto downstream sequence that extended the cdx4 open reading frame by 11 amino acids (GFSSVFQSQSD-stop (SEQ ID NO. 31)). Radiation hybrid (RH) mapping of this foreign sequence placed it 20 cR away from the cdx4 locus. This analysis confirms that the kgg$^{tv205}$ mutant protein is truncated prior to the homeodomain and indicates that the deletion responsible for the mutation is small (~0.5 cM). To provide further evidence that the kgg phenotype is caused by defects in cdx4, we injected wt embryos with cdx4 antisense morpholinos and found that the resulting morphants phenotypically resembled kgg embryos.

We next examined the expression pattern of cdx4 during development. Transcripts for cdx4 are first detected in the early gastrula but become restricted to the posterior-most cells during gastrulation and early somitogenesis. Double whole mount In situ hybridization and sectioning at the 3-somite stage revealed that the cdx4 expression domain initially includes cells in the posterior mesoderm that express scl. However, from the 5-somite stage onward the expression domains of cdx4 and scl are largely non-overlapping. Similar expression profiles were found for the mouse orthologues of cdx4 and Scl during early embryogenesis. At the late primitive streak stage (E7.25), cdx4 transcripts are confined to mesodermal cells of the posterior embryo, the allantois, and the forming yolk sac wall. While cdx4 is not expressed in the nascent blood islands, its expression domain does partially overlap with Scl in mesodermal cells of the posterior primitive streak and the posterior yolk sac. Taken together, these observations are consistent with a conserved, early role for cdx4 during the specification of hematopoietic fate.

Overexpression of cdx4 Induces Ectopic Blood Cells

To further explore the function of cdx4 during embryonic hematopoiesis, we examined the effect of cdx4 overexpression in wt embryos. Embryos injected with cdx4 mRNA (7, 15, or 30 pg) display a range of "posteriorized" phenotypes. In contrast, embryos injected with 15 pg of F(170)L mutant mRNA all exhibit a wt morphology (n=60/60 embryos injected; data not shown). The effect of cdx4 overexpression (15 pg) on blood development was examined at the 5- to 12-somite stages. Surprisingly, 12-20% of the injected embryos showed ectopic scl (n=24/118), gata1 (n=7/59), and fli1 (n=4/26) expression near the midline in a stripe that ran parallel to the endogenous blood precursors. Cross sections revealed that the ectopic scl$^+$ cells were unilaterally located adjacent to the notochord. The reason for this restricted localization is currently unclear, however the genes induced appear specific to the hematopoietic program as ectopic flk1 expression was confined to the upper trunk region (n=11/69), whereas no ectopic expression of pax2.1 was found (n=0/55). In contrast, 11-22% of the injected embryos exhibited decreased expression of scl, gata1, fli1, flk1, and pax2.1. The disrupted tissue development in these embryos may result from abnormal gastrulation, or the conversion of mesoderm to an extreme posterior fate. To assess the ability of cdx4 to rescue kgg$^{tv205}$ mutants, we injected 15 pg of cdx4 mRNA and assayed the number of scl$^+$ and gata1$^+$ cells at the 5- and 10-somite stages, respectively. Consistent with cdx4 being the gene defective in kgg mutants, the hematopoietic defects were partially rescued in approximately 80% of injected mutants (n=15/19 mutants for scl and n=27/33 mutants for gata1).

kgg Mutants have Abnormal hox Gene Expression

In a number of metazoans, caudal homologues have been implicated in AP patterning by regulating the expression of hox genes[38,43-45]. To investigate hox gene expression in kgg mutants we examined the expression of selected hoxb cluster genes and hoxa9a, as many of these hox genes are known to affect haematopoiesis[5]. All of the hox genes examined (hoxb4, hoxb5a, hoxb6b, hoxb7a, hoxb8a, hoxb8b, and hoxa9a) display altered expression patterns in kgg$^{tv205}$ embryos. For instance, the mesodermal expression of hoxb5a normally includes somites two and three, the notochord, and the tailbud region, but in kgg$^{tv205}$ mutants, hoxb5a expression is expanded to include somites two to five, is absent from the notochord, and is reduced in the tailbud. In the case of hoxb6b and hoxa9a, the expression of these hox genes is almost absent in kgg$^{tv205}$ mutants.

Overexpression of hox Genes Rescues Erythropoiesis in kgg Mutants

To further understand how the stripe of hematopoietic/vascular precursors is affected by changes in AP patterning, we examined the scl$^+$ populations in more detail. During normal development, transcripts for scl are first detected around the 3-somite stage in stripes of mesoderm adjacent to the future site of somite six. At the 5-somite stage, de novo expression of scl occurs adjacent to somites one to five. These cells are most likely angioblasts as they express flk1 but not gata1. Transcripts for flk1 and gata1 in cells of the posterior scl$^+$ stripe appear mutually exclusive, suggesting that this stripe is comprised of juxtaposed populations of angioblasts and hematopoietic precursors.

In kgg mutants, there is a preferential loss of gata1$^+$ hematopoietic cells from the posterior stripe with little effect on the adjacent angioblasts. This blood loss in kgg mutants may result, in part, from a posterior shift in the boundary between the anterior (angioblast) and posterior (blood and angioblast) scl$^+$ populations. In support of this, the expression domains of hoxb6b, hoxb7a, and hoxa9a, which share an anterior expression limit with gata1, are significantly reduced in kgg$^{tv205}$ mutants as early as the 3-somite stage. In contrast, the scl$^+$ anterior angioblasts are found rostral to the hoxb7a expression domain but at a similar AP level as hoxb5a. Given that hox gene overexpression can transform cell fates[15] and that a number of hox genes are expressed during mouse yolk sac haematopoiesis[46], we examined whether overexpression of hox paralogues from the 6$^{th}$, 7$^{th}$, 8$^{th}$, or 9$^{th}$ groups were capable of rescuing the blood defect in kgg$^{tv205}$ mutants. Mutants injected with 3 pg of hoxb7a and hoxa9a mRNA displayed an almost complete rescue of gata1$^+$ blood cells at the 18-somite stage (65%; n=13/20 mutants and 100%; n=18/18, respectively), although the axial and tail defects were not rescued. In contrast, the highest non-toxic dose of hoxb6b mRNA (1-2 pg; 64%; n=7/11) led to a small increase in gata1$^+$ blood cells, whereas the highest non-toxic level of hoxb8a mRNA (1-2 pg) failed to rescue the blood defects (n=0/22 mutants; data not shown). Taken together, these findings suggest that the specification of hematopoietic cell fate is dependent upon the proper expression of hox genes such hoxb7a and hoxa9a in the posterior mesoderm and that overexpression of any one of these cdx4 targets can rescue erythropoiesis in kgg mutants.

To provide further evidence that cdx4 and hox genes function together in a common pathway, we examined whether cdx4 overexpression (15 pg) could rescue the expression of hoxb6b, hoxb7a, and hoxa9a in cdx4 morphants. We found a restoration of hoxb6b, hoxb7a, and hoxa9a expression domains in cdx4-rescued morphants. Interestingly, approximately 80% of the injected embryos also displayed ectopic hoxb7a expression in the forebrain and/or hindbrain regions (n=31/39), thus supporting a role for cdx4 in the induction of hox gene expression.

Overexpression of scl Fails to Rescue Erythropoiesis in kgg Mutants

Figure 2:
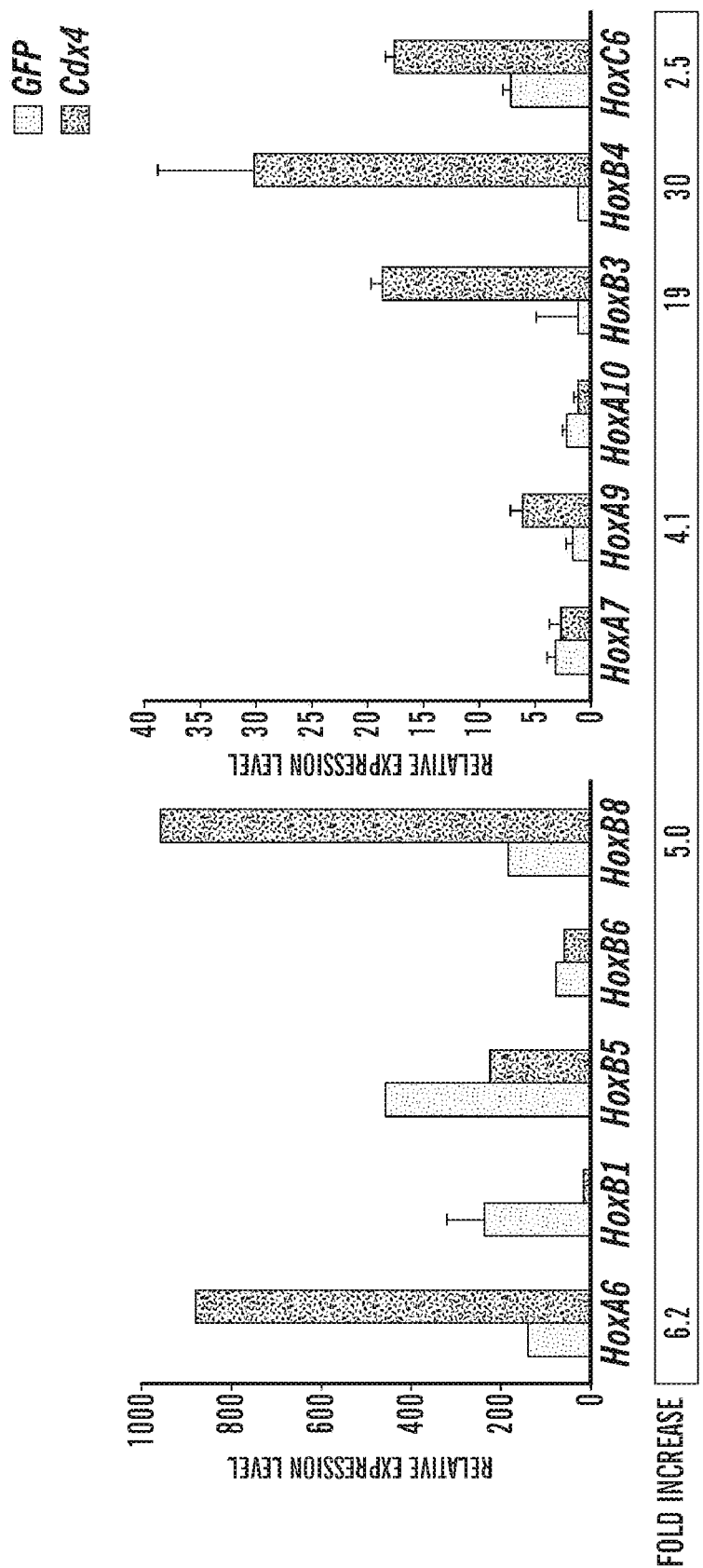

In zebrafish, overexpression of scl leads to an expansion of hematopoietic cells in the posterior lateral plate mesoderm[8]. We examined whether scl overexpression could rescue erythropoiesis in kgg mutants. Wild-type embryos injected with scl mRNA (100 pg), display an expanded number of gata1$^+$ erythroid precursors at the 10 somite stage. In contrast, no such expansion in erythroid cell numbers was found in scl-injected kgg embryos. Given that cdx4 expression precedes that of scl in the posterior mesoderm, our results suggest that the specification of hematopoietic fate by scl is dependent on cdx4.

cdx4 Expands Multipotential Hematopoietic Progenitors Derived from Murine ES Cells Several studies have shown that retroviral expression of Hoxb4 in hematopoietic stem cells or multipotential progenitors enhances the self-renewal/proliferation of these cells[16,19,47]. To examine whether cdx4 has a similar activity, we retrovirally transduced embryoid body (EB) hematopoietic cells with cdx4 and assayed the effect on multilineage hematopoietic colony formation. In this system, cdx4 induced a pronounced expansion of hematopoietic progenitors, including a 13-fold increase in CFU-GEMM (colony forming unit-granulocyte/erythroid/macrophage/megakaryocyte) colonies and a 11-fold increase in CFU-GM colonies compared to GFP-only transduced control cells (FIG. 1). The cdx4-mediated expansion of multilineage progenitors and colony size was more potent than that observed with Hoxb4, which induced a 9-fold increase in CFU-GEMM (FIG. 1). We next examined changes in the expression of selected HoxA, HoxB, and HoxC cluster genes in the cdx4-transduced cells using quantitative PCR. Consistent with the role of cdx4 as a Hox gene regulator, we found widespread alterations in Hox expression levels in cells transduced with cdx4 compared to controls (FIG. 2). Notably, cdx4 induced a marked increase in the expression of HoxB4 (30-fold), HoxB3 (19-fold), HoxB8 (5-fold) and HoxA9 (4.1-fold), all of which have been implicated in hematopoietic stem cell or immature progenitor expansion[18,48,49]. Taken together, these results suggest that cdx4 can enhance the proliferation of early hematopoietic progenitors by up-regulating the expression of target Hox genes.

Figure 3:
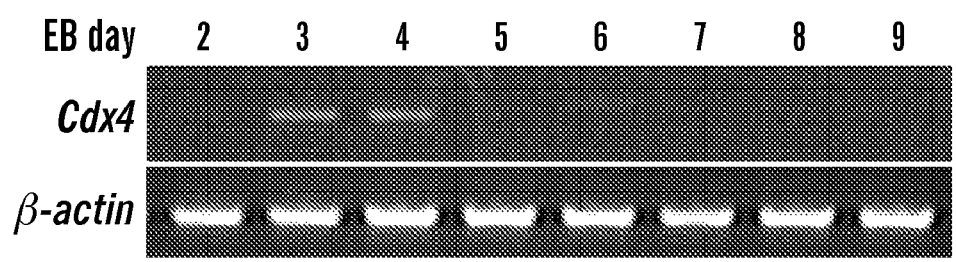
Figure 4:
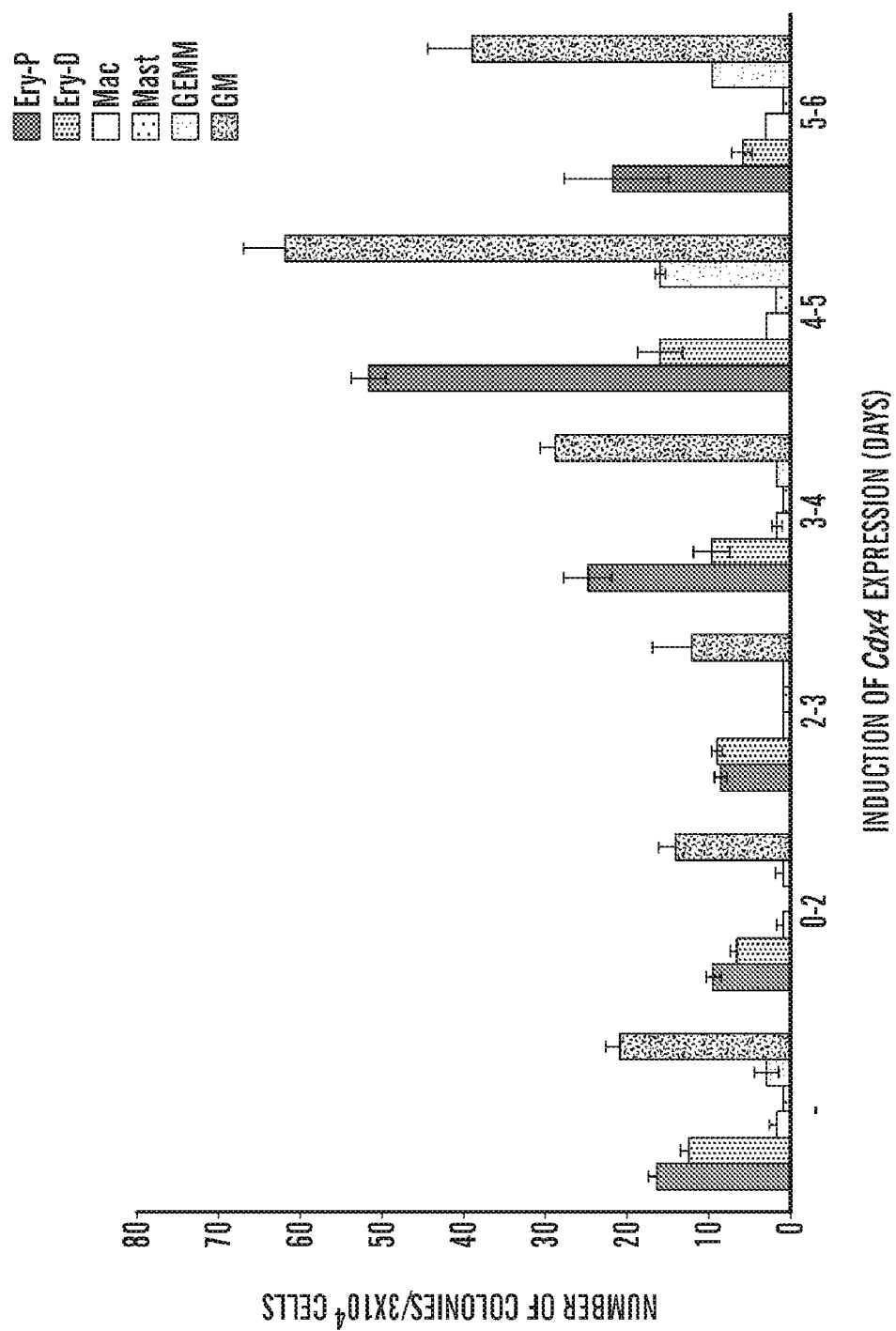

In EBs, precursors committed to primitive and definitive hematopoietic fates arise between day 3 and 4 of differentiation[50]. Consistent with our expression analyses in vivo, we find endogenous expression of cdx4 at day 3 and 4 of EB development (FIG. 3). To more closely investigate the time window during EB differentiation in which cdx4 can enhance multilineage hematopoietic colony formation we engineered ES cells to express cdx4 under the control of a tetracycline-inducible promoter. A 'pulse' of cdx4 expression was induced at different intervals during EB differentiation and hematopoietic colony formation was assayed at day 6 (FIG. 4). The strongest effect of cdx4 overexpression on colony formation was found between day 4 and 5 of EB development with increased multipotent progenitors (CFU-GEMM), CFU-GM, and primitive erythroid colonies compared to uninduced EBs (FIG. 4). These findings are consistent with cdx4 acting at early stages of hematopoietic development to expand the number of multipotential progenitor cells and perhaps, hematopoietic stem cells.

Discussion

Our studies demonstrate that cdx4 is essential for hematopoietic development during vertebrate embryogenesis. Defects in cdx4 lead to an early deficit in scl-expressing hematopoietic precursors, whereas overexpression of cdx4 in zebrafish embryos or mouse ES cells induces blood formation. Loss of cdx4 function is also associated with widespread perturbations in the expression patterns of multiple hox genes. Furthermore, ectopic expression of cdx4 in both zebrafish and mouse cells alters hox gene expression. The rescue of blood development in kgg mutants by overexpressing specific hox genes suggests a pathway in which cdx4 acts upstream of the hox genes to control embryonic blood development.

Figure 5:
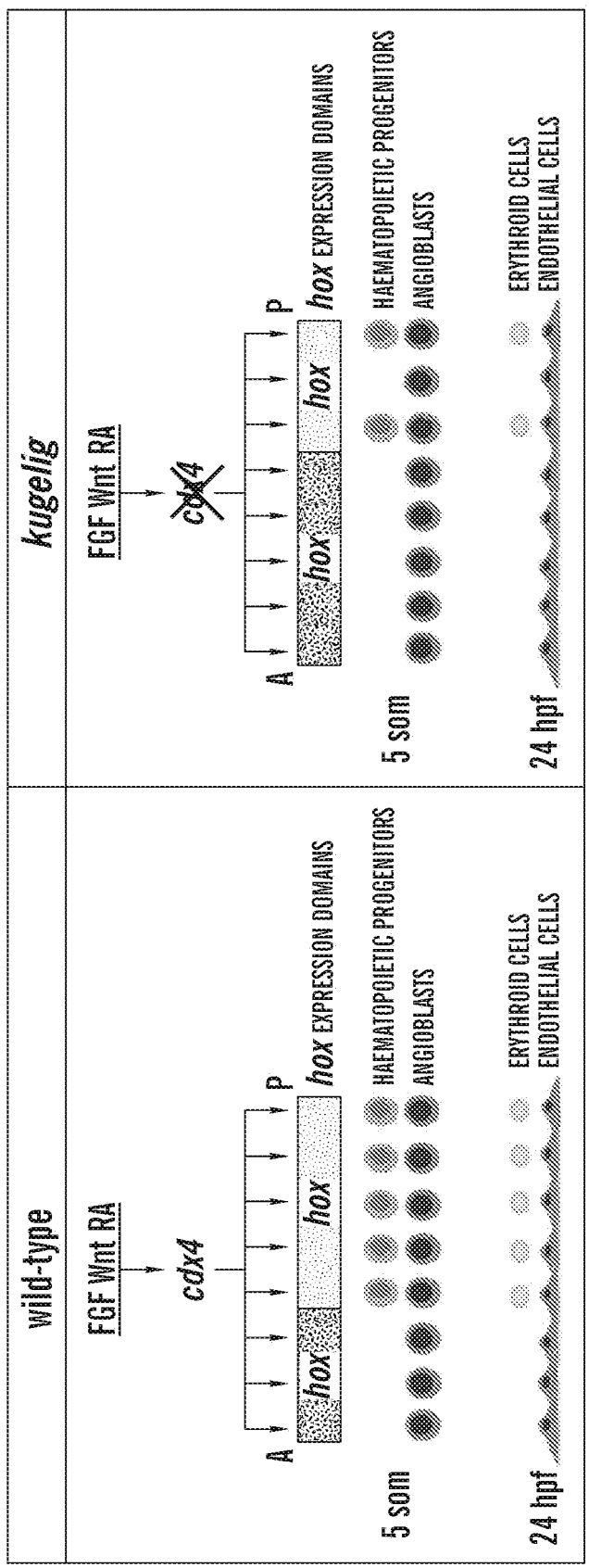

Genetic studies in *Drosophila* led to the proposal that hox genes function in specific combinations to confer tissue identities along the AP axis[1,2]. In kgg mutants, the expression domains of hox genes expressed in the anterior trunk, such as hoxb4 and hoxb5a, are expanded towards the posterior while others such as hoxb6b, hoxb7a and hoxa9a are severely reduced. With regard to the development of ICM precursors, these perturbations in hox expression domains appear to cause a posterior shift in the boundary between the anterior endothelial population and the more posterior populations of blood and endothelial cells. In addition, there is an overall reduction in erythroid cell numbers (schematically represented in FIG. 5). The blood defects in kgg mutants can be restored to almost wild-type levels by overexpressing hoxa9a and hoxb7a, whereas hoxb6b rescues poorly and hoxb8a fails to rescue. These observations suggest that multiple hox genes with redundant activities participate in blood development. In support of this redundancy, the targeted disruption of HoxB6, HoxB7, or HoxA9 in mice does not block early embryonic haematopoiesis[51-53]. Similarly, using morpholinos to knockdown multiple hox genes we have been unable to find single or combinations of hox genes that are required for blood formation during zebrafish development. However, there are technical limitations to this approach as non-specific toxicity makes it difficult to inject more than three morpholinos simultaneously.

Our finding that scl overexpression fails to rescue blood development in kgg mutants suggests that the cdx4-hox pathway may be required to make the posterior lateral plate mesoderm competent to respond to factors that specify hematopoietic fate. In addition to scl, these factors are likely to include other molecules such as BMPs, as we have found that enhancing BMP signaling also fails to rescue the blood defect in kgg mutants. A role for hox genes as 'competence' factors during blood development may explain the restricted localization of ectopic blood cells induced by cdx4 overexpression. Rather than being distributed throughout the embryo, the ectopic blood forms a stripe near the midline that is parallel to the endogenous stripes of hematopoietic precursors. The parallel nature of the cdx4-induced blood cells suggests that the genes responsible for patterning the endogenous stripes may also be responsible for restricting the localization of the ectopic blood. In this model, cdx4 overexpression would induce a combination of hox genes that renders the injected cells competent to respond to other pathways acting upstream of scl. The spatial localization of these signals and the influence of other patterning factors would then account for the restricted stripe of cdx4-induced blood.

Our results have implications for the concept of the hemangioblast, a putative bipotential cell that is thought to express scl and give rise to both blood and vascular lineages in vivo[54]. kgg mutants display a reduced number of scl+ cells with a selective loss of blood but not angioblasts. This finding suggests that if hemangioblasts exist in vivo then they must arise prior to the onset of scl expression and that cdx4 is necessary for this putative population to differentiate into an scl+ hematopoietic precursor. Alternatively, the blood and vascular lineages may arise independently from the posterior mesoderm with cdx4 being required solely for the specification of hematopoietic fate. Either model does not rule out the possibility that early scl+ cells still retain the plasticity to form both blood and vascular lineages if transplanted or cultured in a suitable environment.

Our experiments support a conserved role for cdx4 in the formation of hematopoietic cells during vertebrate embryogenesis. Like the zebrafish orthologue, mouse cdx4 expression overlaps with scl in posterior regions of the conceptus. In addition, cdx4 transcripts are enriched in the Rhodamine-123 low fraction of adult mouse bone marrow, which contains the long term repopulating stem cell (Ihor Lemischka pers. comm.). Overexpression of cdx4 in EBs promotes the formation of multilineage progenitors and alters the expression of multiple Hox genes. The induction of hematopoietic progenitors by cdx4 is similar to that seen with HoxB4 overexpression. Furthermore, cdx4 is able to upregulate the expression of HoxB4 in EBs, raising the possibility that HoxB4 mediates the effect of cdx4 on multilineage progenitor expansion. Given that HoxB4 can also confer upon primitive progenitors the ability to engraft lethally irradiated adults[20], it will be interesting to examine the long-term, multilineage potential of cdx4-expressing progenitors in this assay. Unlike HoxB4, overexpression of cdx4 in EBs leads to significantly more CFU-GM colonies compared to the control. This difference may result from other Hox genes, or combinations of Hox genes, that are induced by cdx4.

Deregulated expression of Hox genes by retroviral activation, chromosomal translocation, or upregulation as a result of mutations in upstream activators have all been implicated in leukemic transformation[5]. The function of cdx genes as transcriptional regulators of hox genes raises the possibility that this family may also participate in leukemogenesis. In support of this, a fusion of CDX2 to TEL/ETV6, a gene frequently rearranged in hematological malignancies, has been found in a patient with acute myeloid leukaemia[55]. CDX2 expression, which is not normally found in hematopoietic cells, was also observed in a case of leukemia lacking the translocation, suggesting that ectopic expression of CDX2 can also occur by other mechanisms[55]. The challenge for future studies will be to better understand how hox genes downstream of cdx genes regulate commitment to a hematopoietic fate and participate in leukemia.

Example 2

Injection of cdx2 morpholinos into kugelig/cdx4 mutants (resulting in cdx2 and cdx4 deficient embryos) results in a complete absence of gata1+ erythroid precursors and a more severe shortening of the embryonic axis at the 10 somite stage. In contrast, vascular progenitors and kidney duct precursors appear to be little, or unaffected, compared to kgg single mutants. Embryos deficient in just cdx2 display normal blood development. Expression of cdx2 and cdx4 overlaps during gastrulation and early somite formation at the time that hematopoietic cells arise during embryogenesis. Taken together, these findings suggest that cdx2 and cdx4 act redundantly during development to control the formation of blood cells.

REFERENCES

The references cited below and incorporated throughout the application are incorporated herein by reference.
1. Lewis, E. A gene complex controlling segmentation in *Drosophila*. Nature 276, 565-570 (1978).

2. Struhl, G. Genes controlling segmental specification in *Drosophila* thorax. Proc. Natl. Acad. Sci. USA 79, 7380-7384 (1982).
3. Hunt, P. & Krumlauf, R. Deciphering the Hox code: clues to patterning branchial regions of the head. Cell 66, 1075-1078 (1991).
4. Buske, C. & Humphries, R. K. Homeobox genes in leukemogenesis. Int. J. Hematol. 71, 301-308 (2000).
5. Owens, B. M. & Hawley, R. G. HOX and Non-Hox Homeobox Genes in Leukemic Hematopoiesis. Stem Cells 20, 364-379 (2002).
6. Galloway, J. L. & Zon, L. I. Ontogeny of hematopoiesis: examining the emergence of hematopoietic cells in the vertebrate embryo. Curr. Top. Dev. Biol. 53, 139-158 (2003).
7. Choi, K., Kennedy, M., Kazarov, A., Papadimitriou, J. C. & Keller, G. A common precursor for hematopoietic and endothelial cells. Development 125, 725-732 (1998).
8. Gering, M., Rodaway, A. R. F., Göttgens, B., Patient, R. K. & Green, A. R. The SCL gene specifies haemangioblast development from early mesoderm. EMBO J. 17, 4029-4045 (1998).
9. Liao, E. C. et al. SCL/Tal-1 transcription factor acts downstream of cloche to specify hematopoietic and vascular progenitors in zebrafish. Genes Dev. 12, 621-6 (1998).
10. Shivdasani, R. A., Mayer, E. L. & Orkin, S. H. Absence of blood formation in mice lacking the T-cell leukemia oncoprotein tal-1/SCL. Nature 373, 432-434 (1995).
11. Robb, L. et al. Absence of yolk sac hematopoiesis from mice with a targeted disruption of the scl gene. Proc. Natl. Acad. Sci. U.S.A. 92, 7075-7079 (1995).
12. Kimmel, C. B. Origin and organization of the zebrafish fate map. Development 108, 581-594 (1990).
13. Warga, R. M. & Nusslein-Volhard, C. Origin and development of the zebrafish endoderm. Development 126, 827-838 (1999).
14. Hammerschmidt, M., Serbedzija, G. N. & McMahon, A. P. Genetic analysis of dorsoventral pattern formation in the zebrafish: requirement of a BMP-like ventralizing activity and its dorsal repressor. Genes Dev. 10, 2452-61 (1996).
15. Krumlauf, R. Hox genes in vertebrate development. Cell 78, 191-201 (1994).
16. Sauvageau, G. et al. Overexpression of HOXB4 in hematopoietic cells causes the selective expansion of more primitive populations in vitro and in vivo. Genes Dev. 9, 1753-1765 (1995).
17. Care, A. et al. Enforced expression of HOXB7 promotes hematopoietic stem cell proliferation and myeloid-restricted progenitor differentiation. Oncogene 18, 1993-2001 (1999).
18. Thorsteinsdottir, U. et al. Overexpression of the myeloid leukemia-associated Hoxa9 gene in bone marrow cells induces stem cell expansion. Blood 99, 121-129 (2002).
19. Antonchuk, J., Sauvageau, G. & Humphries, R. K. HOXB4-induced expansion of adult hematopoietic stem cells ex vivo. Cell 109, 39-45 (2002).
20. Kyba, M., Perlingeiro, R. C. & Daley, G. Q. HoxB4 confers definitive lymphoid-myeloid engraftment potential on embryonic stem cell and yolk sac hematopoietic progenitors. Cell 109, 29-37 (2002).
21. Kroon, E. et al. Hoxa9 transforms primary bone marrow cells through specific collaboration with Meis1a but not Pbx1b. EMBO J. 17, 3714-3725 (1998).
22. Thorsteinsdottir, U. et al. Overexpression of HOXA10 in murine hematopoietic cells perturbs both myeloid and lymphoid differentiation and leads to acute myeloid leukemia. Mol. Cell. Biol. 17, 495-505 (1997).
23. Nakamura, T., Largaespada, D. A., Shaughnessy, J. D. J., Jenkins, N. A. & Copeland, N. G. Cooperative activation of Hoxa and Pbx1-related genes in murine myeloid leukaemias. Nat. Genet. 12, 149-153 (1996).
24. Lam, D. H. & Aplan, P. D. NUP98 gene fusions in hematologic malignancies. Leukemia 15, 1689-1695 (2001).
25. Ziemin-van der Poel, S. et al. Identification of a gene, MLL, that spans the breakpoint in 11q23 translocations associated with human leukemias. Proc. Natl. Acad. Sci. U.S.A. 88, 10735-10739 (1991).
26. Hammerschmidt, M. et al. Mutations affecting morphogenesis during gastrulation and tail formation in the zebrafish, Danio rerio. Development 123, 143-51 (1996).
27. Bennett, C. M. et al. Myelopoiesis in the zebrafish, Danio rerio. Blood 98, 643-651 (2001).
28. Lieschke, G. J., Oates, A. C., Crowhurst, M. O., Ward, A. C. & Layton, J. E. Morphologic and functional characterization of granulocytes and macrophages in embryonic and adult zebrafish. Blood 98, 3087-3096 (2001).
29. Serluca, F. C. & Fishman, M. C. Pre-pattern in the pronephric kidney field of zebrafish. Development 128, 2233-2241 (2001).
30. Krauss, S., Johansen, T., Korzh, V. & Fjose, A. Expression of the zebrafish paired box gene pax[zf-b] during early neurogenesis. Development 113, 1193-1206 (1991).
31. Chong, S. W., Emelyanov, A., Gong, Z. & Korzh, V. Expression pattern of two zebrafish genes, cxcr4a and cxcr4b. Mech Dev. 109, 347-354 (2001).
32. Joly, J. S. et al. Expression of a zebrafish caudal homeobox gene correlates with the establishment of posterior cell lineages at gastrulation. Differentiation 50, 75-87 (1992).
33. Hild, M. et al. The smad5 mutation somitabun blocks Bmp2b signaling during early dorsoventral patterning of the zebrafish embryo. Development 126, 2149-2159 (1999).
34. Postlethwait, J. H. et al. Vertebrate genome evolution and the zebrafish gene map. Nat. Genet. 18, 345-9 (1998).
35. Mlodzik, M., Fjose, A. & Gehring, W. J. Isolation of caudal, a *Drosophila* homeo box-containing gene with maternal expression whose transcripts form a concentration gradient at the pre-blastoderm stage. EMBO J. 4, 2961-2969 (1985).
36. Katsuyama, Y., Sato, Y., Wada, S. & Saiga, H. Ascidian tail formation requires caudal function. Dev. Biol. 213, 257-268 (1999).
37. Edgar, L. G., Carr, S., Wang, H. & Wood, W. B. Zygotic expression of the caudal homolog pal-1 is required for posterior patterning in *Caenorhabditis elegans* embryogenesis. Dev. Biol. 229, 71-88 (2001).
38. Subramanian, V., Meyer, B. I. & Gruss, P. Disruption of the murine homeobox gene cdx1 affects axial skeletal identities by altering the mesodermal expression domains of Hox genes. Cell 83, 641-653 (1995).
39. Chawengsaksophak, K., James, R., Hammond, V. E., Kontgen, F. & Beck, F. Homeosis and intestinal tumours in cdx2 mutant mice. Nature 386, 84-87 (1997).
40. van den Akker, E. et al. cdx1 and cdx2 have overlapping functions in anteroposterior patterning and posterior axis elongation. Development 129, 2181-2193 (2002).
41. Beck, F., Chawengsaksophak, K., Waring, P., Playford, R. J. & Furness, J. B. Reprogramming of intestinal differentiation and intercalary regeneration in cdx2 mutant mice. Proc. Natl. Acad. Sci. U.S.A. 96, 7318-7323 (1999).
42. Tamai, Y. et al. Colonic hamartoma development by anomalous duplication in cdx2 knockout mice. Cancer Res. 59, 2965-2970 (1999).

43. Charité, J. et al. Transducing positional information to the Hox genes: critical interaction of cdx gene products with position-sensitive regulatory elements. Development 125, 4349-4358 (1998).
44. Hunter, C. P., Harris, J. M., Maloof, J. N. & Kenyon, C. Hox gene expression in a single *Caenorhabditis elegans* cell is regulated by a caudal homolog and intercellular signals that inhibit Wnt signaling. Development 126, 805-814 (1999).
45. Isaacs, H. V., Pownall, M. E. & Slack, J. M. W. Regulation of Hox gene expression and posterior development by the *Xenopus* caudal homologue Xcad3. EMBO J. 17, 3413-3427 (1998).
46. McGrath, K. E. & Palis, J. Expression of homeobox genes, including an insulin promoting factor, in the murine yolk sac at the time of hematopoietic initiation. Mol. Reprod. Dev. 48, 145-153 (1997).
47. Buske, C. et al. Deregulated expression of HOXB4 enhances the primitive growth activity of human hematopoietic cells. Blood 100, 862-868 (2002).
48. Bjornsson, J. M. et al. Reduced proliferative capacity of hematopoietic stem cells deficient in hoxb3 and hoxb4. Mol. Cell Biol. 23, 3872-3883 (2003).
49. Perkins, A. C. & Cory, S. Conditional immortalization of mouse myelomonocytic, megakaryocytic and mast cell progenitors by the Hox-2.4 homeobox gene. EMBO J. 12, 3835-3846 (1993).
50. Kennedy, M. et al. A common precursor for primitive erythropoiesis and definitive hematopoiesis. Nature 386, 488-493 (1997).
51. Chen, F., Greer, J. & Capecchi, M. R. Analysis of Hoxa7/Hoxb7 mutants suggests periodicity in the generation of the different sets of vertebrae. Mech. Dev. 77, 49-57 (1998).
52. Kappen, C. Disruption of the homeobox gene Hoxb-6 in mice results in increased numbers of early erythrocyte progenitors. Am. J. Hematol. 65, 111-118 (2000).
53. Lawrence, H. J. et al. Mice bearing a targeted interruption of the homeobox gene HOXA9 have defects in myeloid, erythroid, and lymphoid hematopoiesis. Blood 89, 1922-1930 (1997).
54. Choi, K. The hemangioblast: a common progenitor of hematopoietic and endothelial cells. J. Hematother. Stem Cell Res. 11, 91-101 (2002).
55. Chase, A. et al. Fusion of ETV6 to the caudal-related homeobox gene CDX2 in acute myeloid leukemia with the t(12;13)(p13;q12). Blood 93, 1025-1031 (1999).
56. Kingsley, P. D. et al. Subtractive hybridization reveals tissue-specific expression of ahnak during embryonic development. Dev. Growth Diff. 43, 133-143 (2001).

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

What is claimed is:

1. A method for enhancing proliferation of a mammalian-multipotential hematopoietic progenitor cell comprising, transfecting multipotential hematopoietic progenitor cell in an in vitro culture medium with an exogenous nucleic acid comprising a cdx4 coding sequence operably linked to a promoter.

2. The method of claim 1, wherein the stem cell is a hematopoietic stem cell.

3. The method of claim 1, wherein the cell is a CD34+ cell.

4. The method of claim 1, wherein the cell is autologous.

5. The method of claim 1, wherein the cell is obtained from a human.

6. The method of claim 5, wherein the human is suffering from, or is susceptible to, decreased blood cell levels.

7. The method of claim 6, wherein the decreased blood cell levels are caused by chemotherapy, radiation therapy, bone marrow transplantation therapy or congenital anemia.

8. The method of claim 1, wherein the exogenous nucleic acid is a retroviral vector.

9. The method of claim 1, wherein the exogenous nucleic acid is an episomal vector.

10. The method of claim 1, wherein the stem cell is an embryonic stem cell.

11. A method of treating a mammal in need of improved hematopoietic capability, comprising the steps of:
  (a) tranfecting a plurality of multipotential hematopoietic progenitor cells removed from the mammal with exogenous nucleic acid comprising a cdx4 sequence;
  (b) culturing said tranfected multipotential hematopoietic progenitor cells to form an expanded population of cells; and
  (c) returning said expanded population of cells to the mammal, whereby hematopoietic capability is improved.

12. The method of claim 11, wherein the mammal is a human.

13. The method of claim 11, wherein the exogenous nucleic acid is a retroviral vector.

* * * * *

SEQUENCE LISTING

```
<160> NUMBER OF SEQ ID NOS: 31

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agctcctttt ggactattac                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccaacgtaca tgatttggaa                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 3 atacctttg gagaaagagg                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccggttgatg acgactggac                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caaaacgaga acgaaggaga                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acctgtctct ctgaaagccc                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
taagatctgg tttcagaacc                                                   20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggatgatcc aagttcgagt                                                   20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

-continued

```
agcctcggac ctccaaattc                                              20

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
gagaaattta tattgt                                                  16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
gagaaatcca tattgt                                                  16

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgcgaattc cccatgagtt cctatttcgt ca                                32

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atgcgaattc accatgagtt cattgtatta tgcg                              34

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atgcgaattc accatgagct catatttcgt caac                              34

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgcgaattc accatgtcga catccggagc t                                 31
```

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcatctcgag ctacattcta catgttatgt ac                                32

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gactctcgag ctactcatca tcttcttctt c                                 31

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcatctcgag ctacatttgt tttgccttgt c                                 31

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gatctctaga ttagtcttcc ttcgtttc                                     28

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgtacatgat ttggaagaaa cccct                                        25

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
catgtacgtt ggatacctttt tgg                                         23

<210> SEQ ID NO 22

-continued

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tccacaaccc acgcctctta tt                                          22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aggcgtgggt tgtggattac                                             20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gatacactca ccacatacag                                             20

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtgatcaaca acacgtcc                                               18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggaatctcct gtcagctg                                               18

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atgcgaattc accatggcca tgagttccta tttg                             34

<210> SEQ ID NO 28
<211> LENGTH: 31
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 28
gcatctcgag ctatagactt ggcggaggtc c                                    31

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atgcgaattc accatgagtt cctacttcgt caat                                 34

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcatctcgag ctatttagaa ttgctagaag c                                    31

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Phe Ser Ser Val Phe Gln Ser Gln Ser Asp
 1               5                  10
```